United States Patent
Govari et al.

(10) Patent No.: US 12,239,465 B2
(45) Date of Patent: Mar. 4, 2025

(54) BALLOON CATHETER WITH DIAGNOSTIC ELECTRODES, FAR FIELD DETECTION ELECTRODES, AND GUIDEWIRE

(71) Applicant: Biosense Webster (Israel) Ltd., Yokneam (IL)

(72) Inventors: Assaf Govari, Haifa (IL); Vadim Gliner, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 18/309,081

(22) Filed: Apr. 28, 2023

(65) Prior Publication Data

US 2023/0255562 A1    Aug. 17, 2023

Related U.S. Application Data

(63) Continuation of application No. 16/553,066, filed on Aug. 27, 2019, now Pat. No. 11,660,050.

(Continued)

(51) Int. Cl.
*A61B 18/18*    (2006.01)
*A61B 5/00*    (2006.01)
(Continued)

(52) U.S. Cl.
CPC ............ *A61B 5/6853* (2013.01); *A61B 5/287* (2021.01); *A61B 5/361* (2021.01); *A61B 5/6859* (2013.01); *A61M 25/09* (2013.01)

(58) Field of Classification Search
CPC ...... A61B 18/1492; A61B 2018/00214; A61B 2018/0022; A61B 2018/00351;
(Continued)

(56) References Cited

U.S. PATENT DOCUMENTS 6,405,067 B1    6/2002    Mest et al.
9,655,677 B2    5/2017    Salahieh et al.
(Continued)

FOREIGN PATENT DOCUMENTS

CN    107847173 A    3/2018
JP    2017516588 A    6/2017
(Continued)

OTHER PUBLICATIONS

Extended European Search Reported dated Jul. 14, 2020, from European Application No. 19204352.9.
(Continued)

*Primary Examiner* — Joseph A Stoklosa
*Assistant Examiner* — Brian M Antiskay

(57) ABSTRACT

A medical apparatus includes a shaft, an expandable frame, a membrane, a diagnostic electrode, a reference electrode, and a processor. The shaft is configured for insertion into an organ of a patient. The expandable frame is coupled to a distal end of the shaft. The diagnostic electrode, which is disposed on an external surface of the expandable frame, is configured to sense diagnostic signals when in contact with tissue. The reference electrode is disposed on a surface of the expandable frame directly opposite the diagnostic electrode, wherein the reference electrode is electrically insulated from the tissue and is configured to sense interfering signals.

16 Claims, 4 Drawing Sheets

Related U.S. Application Data

(60) Provisional application No. 62/750,461, filed on Oct. 25, 2018.

(51) Int. Cl.
*A61B 5/287* (2021.01)
*A61B 5/361* (2021.01)
*A61M 25/09* (2006.01)

(58) Field of Classification Search
CPC .. A61B 2018/0016; A61B 2018/00839; A61B 2018/00267; A61B 5/287; A61B 2018/00875; A61B 2018/1467; A61B 2017/00022; A61B 2017/00044; A61B 1/00085; A61B 5/6858; A61B 8/445
USPC ........ 600/372–374, 377, 381, 393, 434–435, 600/466, 508–509
See application file for complete search history.

(56) References Cited

U.S. PATENT DOCUMENTS

| | | | |
|---|---|---|---|
| 10,722,141 B2 | 7/2020 | Gliner | |
| 10,974,031 B2 | 4/2021 | Govari et al. | |
| 2002/0151807 A1 | 10/2002 | Goldin | |
| 2012/0296232 A1 | 11/2012 | Ng | |
| 2014/0025069 A1 | 1/2014 | Willard et al. | |
| 2015/0141982 A1 | 5/2015 | Lee | |
| 2015/0351652 A1 | 12/2015 | Marecki et al. | |
| 2015/0366508 A1 | 12/2015 | Chou et al. | |
| 2016/0317093 A1 | 11/2016 | Berenfeld et al. | |
| 2017/0027465 A1* | 2/2017 | Blauer | A61B 5/6858 |
| 2017/0143201 A1 | 5/2017 | Claude et al. | |
| 2017/0172442 A1 | 6/2017 | Govari | |
| 2017/0354364 A1* | 12/2017 | Bar-Tal | A61B 5/7445 |
| 2018/0146948 A1 | 5/2018 | Chou et al. | |
| 2018/0184982 A1 | 7/2018 | Basu et al. | |
| 2018/0199976 A1 | 7/2018 | Fischer | |

FOREIGN PATENT DOCUMENTS

| | | |
|---|---|---|
| JP | 2018108376 A | 7/2018 |
| JP | 2018524085 A | 8/2018 |
| WO | 2015/117908 A1 | 8/2015 |

OTHER PUBLICATIONS

English translation of Search Report dated May 31, 2023, from corresponding Japanese Application No. 2019-193273.
English translation of Notification of Reasons for Refusal dated Jun. 6, 2023, from corresponding Japanese Application No. 2019-193273.
English translation of Written Opinion dated Sep. 5, 2023, from corresponding Japanese Application No. 2019-193273.
Search Report (Communication Pursuant to Art. 94(3) EPC) dated Sep. 6, 2023, from European Application No. 19204352.9.
English translation of Notification of Reasons for Refusal dated Nov. 7, 2023, from corresponding Japanese Application No. 2019-193273.
English translation of First Office Action dated Nov. 16, 2023, from corresponding Chinese Application No. 201911022761.6.
English translation of Written Opinion dated Feb. 6, 2024, from Japanese Application No. JP2019193273.
English translation of Decision to Grant a Patent dated Feb. 20, 2024, from Japanese Application No. JP2019193273.
English translation of Second Office Action dated Mar. 26, 2024, from corresponding Chinese Application No. 201911022761.6.
English translation of Notification to Grant Patent dated May 16, 2024, from corresponding Chinese Application No. 201911022761.6.

* cited by examiner

BALLOON CATHETER WITH DIAGNOSTIC ELECTRODES, FAR FIELD DETECTION ELECTRODES, AND GUIDEWIRE

PRIORITY AND CROSS-REFERENCE TO RELATED APPLICATIONS

This application is a continuation application under 35 U.S.C. § 120 of U.S. patent application Ser. No. 16/553,066 filed Aug. 27, 2019, which claims the benefit of priority from U.S. Provisional Patent Application No. 62/750,461, filed Oct. 25, 2018. This application is related to a U.S. patent application Ser. No. 16/170,631 filed Oct. 25, 2018, entitled "ELECTRODES ON DOUBLE-SIDED PRINTED CIRCUIT BOARD (PCB) TO CANCEL FAR-FIELD SIGNAL,", and to a U.S. patent application Ser. No. 16/170,661 filed Oct. 25, 2018 entitled "COMBINED ACTIVE CURRENT LOCATION (ACL) and TISSUE PROXIMITY INDICATION (TPI) SYSTEM,". The disclosures of all referenced patent applications are incorporated herein by reference.

FIELD OF THE INVENTION

The present invention relates generally to medical probes, and particularly to catheters for electrophysiological procedures.

BACKGROUND OF THE INVENTION

Various known catheter designs have an expandable frame, which may be disposed with devices, fitted at their distal end. For example, U.S. For Patent Application Publication 2017/0172442 describes cardiac catheterization that is performed with a catheter having a basket-shaped assembly at its d distal end. A plurality of spline electrodes is disposed on the splines of the assembly. The assembly is configurable in an expanded arrangement wherein the splines bow radially outwardly and in a collapsed arrangement, wherein the splines are arranged generally along the longitudinal axis of the catheter body. A far-field electrode is disposed in the interior of the assembly. An intracardiac electrogram and a far-field electrogram are obtained with at least one of the spline electrodes and the far-field electrode, respectively. The far-field component is removed from the intracardiac electrogram using the far-field electrogram.

As another example, U.S. Pat. No. 9,655,677 describes cardiac tissue ablation catheters including an inflatable and flexible toroidal or spherically shaped balloon disposed at a distal region of an elongated member. A flexible circuit is carried by an outer surface of the balloon, the flexible circuit including, a plurality of flexible branches conforming to the radially outer surface of the balloon, each of the plurality of flexible branches including a substrate, a conductive trace carried by the substrate, and an ablation electrode carried by the substrate. The ablation electrode is in electrical communication with the conductive trace, and an elongated shaft comprising a guidewire lumen extending in the elongated member and extending from a proximal region of the inflatable balloon to distal region of the inflatable balloon and being disposed within the inflatable balloon, wherein a distal region of the elongated shaft is secured directly or indirectly to the distal region of the inflatable balloon.

U.S. Patent Application Publication 2015/0366508 describes a flex-PCB catheter device that is configured to be inserted into a body lumen. The flex-PCB catheter comprises an elongate shaft, an expandable assembly, a flexible printed circuit board (flex-PCB) substrate, a plurality of electronic components and a plurality of communication paths. The elongate shaft comprises a proximal end and a distal end. The expandable assembly is configured to transition from a radially compact state to a radially expanded state. The plurality of electronic elements is coupled to the flex-PCB substrate and are configured to receive and/or transmit an electric signal. The plurality of communication paths is positioned on and/or within the flex-PCB substrate. The communication paths selectively couple the plurality of electronic elements to a plurality of electrical contacts configured to electrically connect to an electronic module configured to process the electrical signal. The flex-PCB substrate can have multiple layers, including one or more metallic layers. Acoustic matching elements and conductive traces can be included in the flex-PCB substrate.

U.S. Patent Application Publication 2018/0199976 describes a catheter device for ablating biological material. The catheter device comprises a first electrode and a second electrode, and an interface. A first lead electrically connects the first electrode with the interface, and a second lead electrically connects the second electrode with the interface. The interface is configured for electrically connecting the first lead and the second lead with a measurement device for electrically stimulating the first electrode and the second electrode and for detecting an electric quantity being associated with an electric response of a biological material being located in between the two stimulated electrodes. In an embodiment, locating the electrode pair close to each other reduces a far field potential and thus contributes to avoiding unintentional stimulation of the tissue outside a lesion.

Catheter tip designs were proposed with a recessed electrode to detect far-field signals. For example, U.S. Pat. No. 6,405,067 describes a catheter particularly suitable for bipolar mapping and ablating comprises an elongated flexible body having a distal region and at least one lumen extending therethrough. A tip electrode is mounted on the distal region. A ring electrode is mounted on a recessed central region. The ring electrode has an outer diameter less than the outer diameters of the exposed distal region and a proximal region. With this design, the exposed region of the tip electrode is in direct contact with the heart tissue, and thus senses both the local activation energy (near-field signals) at the point of contact with the heart tissue and far field activation energy (far-field signals) received by the exposed region through the blood. However, the recessed ring electrode is protected from direct contact with the heart tissue, but does contact with surrounding blood. The close proximity of the recessed electrode to the exposed region enables the recessed electrode to receive approximately the same far-field signals as the exposed region. However, the recessed electrode does not pick up the local activation potential (near-field signals) that are received by the exposed region. This design permits the creation of high resolution electrograms.

As another U.S. example, Patent Application Publication 2002/0151807 describes a method for measuring near-field electrical activity at a location in a heart comprising introducing into the heart a catheter. The catheter comprises an elongated tubular body having a distal region and a circumferential recess along the length of the distal region, a first electrode mounted on the distal region in close proximity to the circumferential recess, and a second electrode mounted within the circumferential recess. The distal region is positioned at the location in the heart so that the first electrode is in direct contact with heart tissue and the second electrode is not in direct contact with heart tissue but is in contact with blood. A first signal is obtained with the first electrode, and a second signal is obtained with the second electrode. The first signal and the second signal are compared to obtain the near-field electrical activity at the location in the heart.

SUMMARY OF THE DISCLOSURE

A medical apparatus includes a shaft, an expandable frame, a membrane, a diagnostic electrode, a reference electrode, and a processor. The shaft is configured for insertion into an organ of a patient. The expandable frame is coupled to a distal end of the shaft and extends along a longitudinal axis, wherein the expandable frame includes a plurality of expandable spines disposed about the longitudinal axis to define an internal lumen. The membrane is disposed inside the internal lumen defined by the plurality of spines. The diagnostic electrode, which is disposed on an external surface of the expandable frame, is configured to sense diagnostic signals when in contact with tissue. The reference electrode is disposed on a surface of the expandable frame directly opposite the diagnostic electrode, wherein the reference electrode is electrically insulated from the tissue and is configured to sense interfering signals. The processor is configured to: (a) receive the diagnostic signals sensed by the diagnostic electrode, (b) receive the interfering signals sensed by the reference electrode, and (c) calculate corrected diagnostic signals by subtracting the interfering signals from the diagnostic signals.

In some embodiments, the reference electrode is in direct contact with the membrane to define a gap between the spines and the membrane so that the reference electrode is in contact with blood flow but not in contact with tissue to detect far field signals conducted by blood.

In some embodiments, at least an expandable spine from among the expandable spines is made of flexible printed circuit board (PCB), and wherein the diagnostic electrode and the reference electrode are disposed on opposing facets of the flexible PCB.

In an embodiment, the shaft and the membrane are hollow along a longitudinal axis thereof, and wherein the medical probe further includes a guidewire configured to be inserted through the shaft and the balloon, and to guide the balloon toward a target location in the organ.

In another embodiment, the interfering signals include far-field bio-electrical signals.

There is additionally provided, in accordance with an embodiment of the present invention, a method, including inserting into an organ of a patient a medical probe, including an expandable frame coupled to a distal end of the shaft, the expandable frame extending along a longitudinal axis, wherein the expandable frame includes a plurality of expandable spines disposed about the longitudinal axis to define an internal lumen, and wherein a membrane is disposed inside the internal lumen. Diagnostic signals are sensed with a diagnostic electrode, which is disposed on an external surface of the expandable frame, wherein the diagnostic electrode is configured to sense diagnostic signals when in contact with tissue. Interfering signals are sensed with a reference electrode, which is disposed on a surface of the expandable frame directly opposite the diagnostic electrode, wherein the reference electrode is electrically insulated from the tissue. The diagnostic signals sensed by the diagnostic electrode, and the interfering signals sensed by the reference electrode, are received in a processor. Corrected diagnostic signals are calculated by subtracting the interfering signals from the diagnostic signals.

The present invention will be more fully understood from the following detailed description of the embodiments thereof, taken together with the drawings in which:

DETAILED DESCRIPTION OF EMBODIMENTS

Overview

Figure 1:
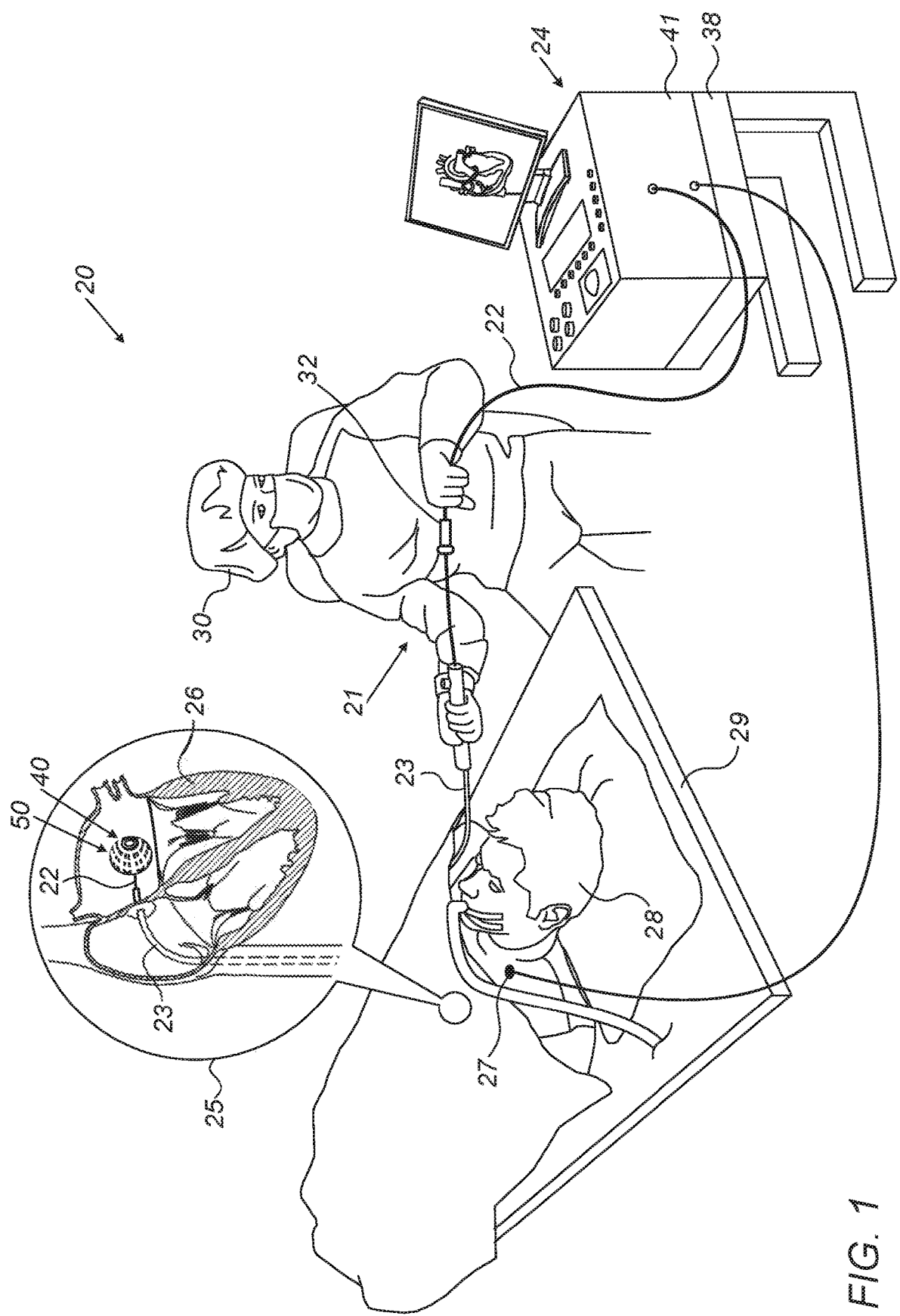
FIG. 1 is a schematic, pictorial illustration of a catheter-based cardiac diagnostic system comprising a diagnostic balloon, in accordance with an embodiment of the present invention.

Diagnostic electrophysiological (EP) signals may be acquired from a tissue region in the heart using an electrode of a catheter in physical contact with the tissue region. Yet, in acquiring such EP signals from the tissue region, there are typically interfering signals, which may include far field signals from regions distant from the tissue region.

In a normally functioning heart, the diagnostic EP signals and the far-field interfering signals may be readily distinguished because the different signals arrive at the acquiring diagnostic electrode at different times. However, if the heart exhibits atrial fibrillation, the signals from atrial tissue and the far-field signals may overlap.

For example, if the tissue region is in an atrium, the interfering signals that are the most evident are typically bio-electric signals emanating from a ventricle (referenced herein as "far-field" signals). Such far-field ventricular bio-electric signals are relatively strong compared to the atrial signals, and the overlap of signals makes it difficult or impossible to identify and/or analyze diagnostic atrial signal.

Hence, we have devised various embodiments of the present invention that are described hereinafter that allow for reducing if not eliminating the far-field signal. To achieve this, we have devised catheters for insertion into an organ, such as a heart, of a patient, which comprise a correlated arrangement of diagnostic electrodes and reference electrodes. In some embodiments, the catheters are disposed with pairs of diametrically opposing sensing electrodes, each pair comprising a diagnostic electrode and a reference electrode.

The diagnostic electrode acquires intra-cardiac EP signals from tissue it physically contacts. As noted above, in addition to acquiring diagnostic EP signals, such as intra-cardiac electrocardiogram (ECG) signals, the diagnostic electrode may also receive interfering electromagnetic signals, such as far-field bio-electric signals and radiofrequency and/or electrical-frequency signals. Yet, the directly opposing reference electrode, which is electrically insulated from tissue, acquires only the interfering signals. In an embodiment, a processor uses the signals acquired by the reference electrode to subtract any interfering signals received d by the respective diagnostic electrode.

In the present context, a far-field bio-electric signal is a signal from a region distant from the contacted tissue region. Typically, such far-field bio-electric signal propagates by conduction through blood and, as noted above, is sensed both by the diagnostic electrode that in contact with tissue (that in parallel senses a "near-field signal") and by the opposing reference electrode.

In some embodiments, the diagnostic electrode is disposed over on an external surface of a flexible printed circuit board (PCB) strip of an expandable frame of a catheter such as a basket catheter or a balloon catheter. The respective reference electrode is disposed directly opposite to the diagnostic electrode, on an internal surface of the PCB strip (i.e., inside a volume the catheter confines), and is electrically isolated from tissue but electrically contacts intracardiac blood.

In some embodiments, the PCB strips (with pairs of diagnostic and reference electrodes disposed on opposing facets of each flexible PCB strip) are, for example, assembled to form an expandable frame, for example, of a basket catheter. In other embodiments, the PCB strips (with the aforementioned pairs of electrodes) are cemented to an exterior surface of a balloon membrane, as described below. With either type of catheter, as the catheter is moved, a diagnostic electrode repeatedly contacts different tissue regions and acquires tissue EP signals and far-field signals, the corresponding directly opposing reference electrodes only acquire the far-field signals. Thus, subtraction of the second electrode signal from the first electrode signal leaves essentially just the tissue signal.

In some embodiments, a guidewire is provided with a balloon catheter, that traverses the interior of the balloon membrane along its axis, via, for example, a hollow shaft to which a hollow membrane of a balloon is fitted, the membrane being hollow along a longitudinal axis defined by the shaft. In a medical procedure, the guidewire is typically navigated to a target location of suspected aberrant EP activity in the heart, such as to an ostium of a pulmonary vein. The guidewire is configured to allow the hollow shaft and the hollow membrane of the balloon to slide over the guidewire so that the balloon can be shifted (e.g., advanced) in order to contact target tissue (i.e., target location in the organ).

In an embodiment, during such catherization procedure, the guidewire is first navigated to a desired target in an organ (e.g., to an ostium in the left atrium of the heart). Then the balloon, still in a deflated form, is advanced along the guidewire until it is in a desired position, and then the balloon is inflated so that the diagnostic electrodes disposed at the exterior of the balloon contact target tissue to sense diagnostic EP signals.

In some embodiments, the balloon is additionally configured to have a smooth distal edge, e.g., with no protruding distal "knob" that may contribute to the formation of blood clots. A completely round and smooth balloon structure presents less probability of blood clot formation and/or irritation of tissue of a cardiac chamber. Even with the above described guidewire, there are very few protuberances which may cause blood clots.

Typically, the processor is programmed in software containing a particular algorithm that enables the processor to conduct each of the processor related steps and functions outlined above.

The disclosed catheters, with their electrode pairs that cancel interfering far-field signals, and, in case of a balloon catheter, rounded exterior that reduces risk of formation of blood clots, may provide improved EP diagnostics at a lower risk of side effects, such as a stroke.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

System Description

FIG. 1 is a schematic, pictorial illustration of a catheter-based cardiac diagnostic system 20 comprising a diagnostic balloon 40, in accordance with an embodiment of the present invention. System 20 comprises a catheter 21, wherein, as seen in an inset 25, a distal end of shaft 22 of the catheter is inserted through a sheath 23 into a heart 26 of a patient 28 lying on a table 29. The proximal end of catheter 21 is connected to a control console 24. In the embodiment described herein, diagnostic balloon 40 carries diagnostic electrodes 50 for electrophysiological diagnostic purposes, such as sensing arrhythmia activity in tissue inside heart 26.

Physician 30 navigates the distal end of shaft 22 to a target location in heart 26 by manipulating shaft 22 using a manipulator 32 near the proximal end of the catheter and/or deflection from the sheath 23. During the insertion of shaft 22, balloon 40 is maintained in a collapsed configuration by sheath 23. By containing balloon 40 in a collapsed configuration, sheath 23 also serves to minimize vascular trauma along the way to target location.

To track positions of diagnostic electrodes 50, a plurality of external electrodes 27 is coupled to the body of patient 28; for example, three external electrodes 27 may be coupled to the patient's chest, and another three external electrodes may be coupled to the patient's back. (For ease of illustration, only one external electrode is shown in FIG. 1.) In some embodiments, diagnostic electrodes 50 sense potentials induced in heart 26 by applying voltages between pairs of external electrodes 27.

Similar techniques used for tracking the locations of diagnostic electrodes 50 inside heart 26, as described above, is described in U.S. patent application Ser. No. 15/966,514, filed Apr. 30, 2018, entitled "Improved Active Voltage Location (AVL) Resolution," which is assigned to the assignee of the present patent and whose disclosure is incorporated herein by reference.

Based on the potentials sensed by electrodes 50 and given the known positions of external electrodes 27 on the patient's body, processor 41 calculates an estimated location of at least a portion of electrodes 50 within the patient's heart. Processor 41 may thus associate any given signal received from diagnostic electrodes 50, such as an electrophysiological signal, with the location at which the signal was acquired.

Control console 24 comprises a processor 41, typically a general-purpose computer, with suitable front end and interface circuits 38 for receiving signals from catheter 21, as well as for applying treatment via catheter 21 in heart 26 and for controlling the other components of system 20. Processor 41 typically comprises a general-purpose computer with software programmed to carry out the functions described herein. The software may be downloaded to the computer in electronic form, over a network, for example, or it may, alternatively or additionally, be provided and/or stored on non-transitory tangible media, such as magnetic, optical, or electronic memory.

In particular, processor 41 runs a dedicated algorithm that enables processor 41 to perform the disclosed steps, comprising calculations of the locations and respective proximities.

The example configuration shown in FIG. 1 is chosen purely for the sake of conceptual clarity. The disclosed techniques may similarly be applied using other system components and settings. For example, system 20 may comprise other components and perform non-cardiac diagnostics.

Expandable Frame Carrying Diagnostic and Far-Field Sensing Electrodes

Figure 2A:
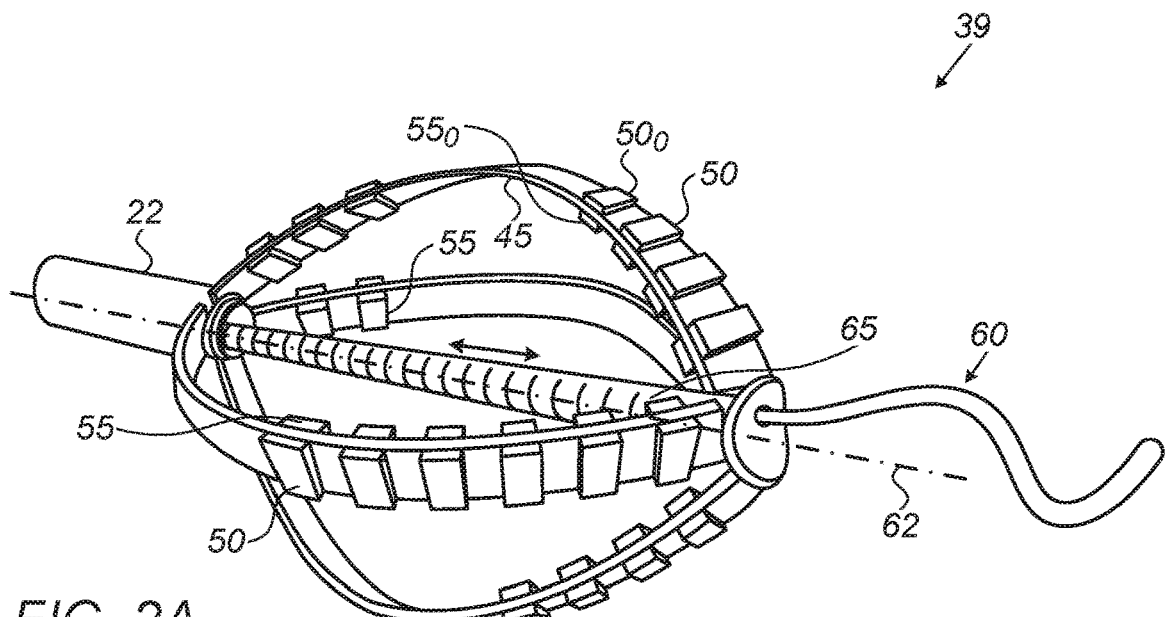
FIGS. 2A and 2B are schematic pictorial illustrations of an expandable frame carrying diagnostic electrodes and far-field sensing electrodes, in accordance with embodiments of the present invention.
Figure 2B:
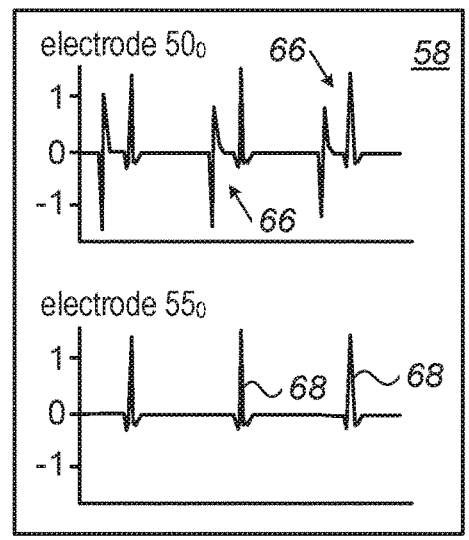

FIGS. 2A and 2B are schematic pictorial illustrations of an expandable frame 39 carrying diagnostic electrodes 50 and far-field sensing electrodes 55, in accordance with embodiments of the present invention.

As seen, an expandable frame 39 extends from shaft 22 and is connected to a distal end 65 of shaft 22, with expandable frame 39 extending along a longitudinal axis 62 and comprising a plurality of expandable spines 45 disposed about longitudinal axis 62 to define an internal lumen, such as one defined by a surface of revolution about longitudinal axis 62, yet, in general the internal lumen is not required to have rotational symmetry. Distal end 65 of shaft 22 can slide on a guidewire 60, as described below.

In some embodiments, at least an expandable spine from among expandable spines 45 is made of flexible PCB. In an embodiment, expandable spines 45 are all comprising flexible PCB spines. The expandable spines 45 can be connected to each other at the respective ends of each spine 45 or the spines can be connected to shaft 22 at one end of each spine and distal end 65 of the other end of each spine. FIG. 2A shows a plurality of diagnostic electrodes 50 that is disposed over PCB spines 45 exterior. When catheter 40 is applied to acquire diagnostic EP signals from tissue, electrodes 50 contact both tissue and blood, and acquire both diagnostic near-field signals and interfering far-field signals due to each electrode facing away from the longitudinal axis 62. A respective plurality of far-field detecting directly opposing electrodes 55 can be distinguished as facing an internal volume defined by the surface of revolution about longitudinal axis 62. Specifically, each far-field electrode 55 can be disposed such that the sensing surface of each electrode faces toward the longitudinal axis 62. Each reference electrodes 55 opposing a respective diagnostic electrode 50 comes in contact only with blood, and acquire only the respective interfering far-field signals conducted by blood. While each far-field electrode 55 is shown directly opposite that of the diagnostic electrode 50, it is within the scope of this invention to have some or even all of electrodes 50 offset with far-field electrodes 55.

Inset 58 of FIG. 2A shows an example of a bio-electrical signal 66 that an electrode 500 acquires when in physical contact with cardiac tissue. Bio-electrical signal 66 comprises a diagnostic signal and an interfering signal, as electrode 500 acquires at a same time both a near-field diagnostic signal, and a far-field signal that is unrelated to the EP activity at the contacted tissue. Reference electrode 550, which is located opposite to diagnostic electrode 500, at a very close proximity to electrode 500, is electrically isolated from tissue and acquires only an interfering far-field signal 68. Thus, simple subtraction of signal 68 from signal 66 leaves just the tissue EP signal.

In an embodiment, one or more leads to diagnostic electrodes 50 include vias in the PCB stripes if spines 45, for example, in order to minimize extra footprint and/or electrical noises associated with the leads.

As noted above, the catheter shown in FIG. 2A further comprises a hollow distal end 65 for frame 39 (e.g., a movable edge of the catheter inside hollow shaft 22) to slide on a guidewire 60 to access tissue in confined cardiac regions such as that of an ostium of a pulmonary vein. Distal end 65 can be retracted or pushed from a handle of the catheter through hollow shaft 22 so as to expand or collapse frame 39, respectively.

In an alternative embodiment, the far-field signal acquiring electrode on the inside of each PCB 45 spine is a single large electrode 155, as seen in FIG. 2B. As seen, single reference electrode 155 is disposed over an entire surface of the expandable spine. Such an alternative embodiment may be desired if, for example, the far field signal collected by small electrodes 55 is too noisy to be useful. In an embodiment, electrode 155 is formed by electrically connecting the plurality of reference electrodes 55 disposed on the spine with each other.

The illustration shown in FIG. 2B is chosen purely for the sake of conceptual clarity. For example, in an alternative embodiment, the inner side of each PCB comprises several far-field detecting electrodes that are each larger than an electrode 55 and smaller than an electrode 155.

Figure 3:
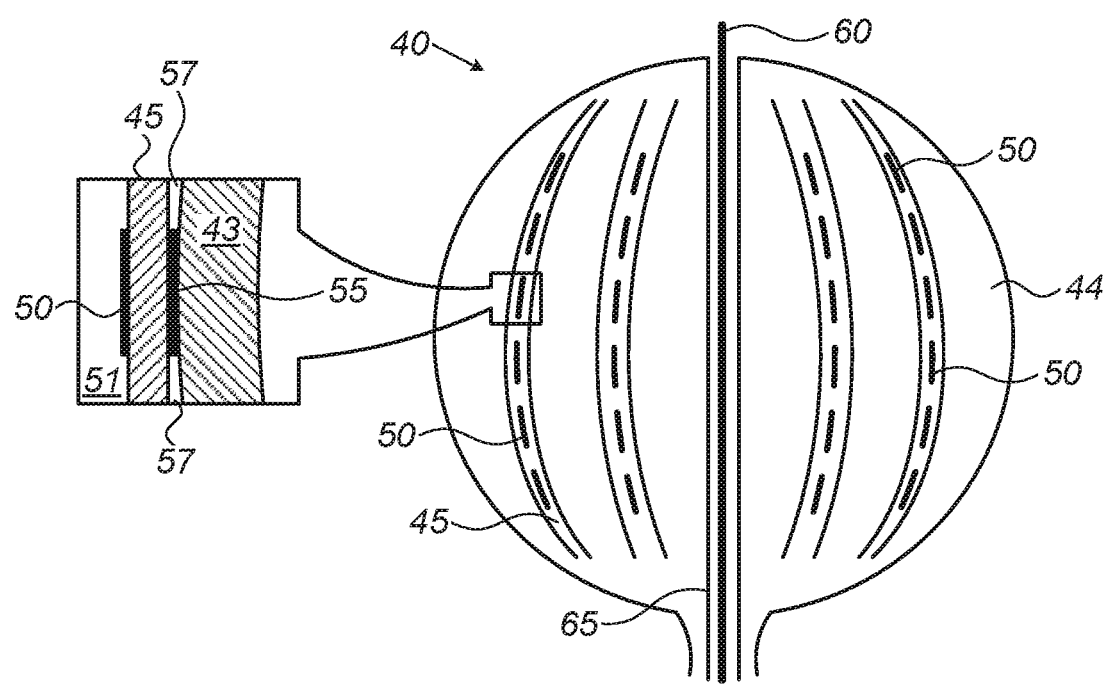
FIG. 3 is a schematic pictorial illustration of the diagnostic balloon catheter of FIG. 1, in accordance with an embodiment of the present invention.

Balloon Catheter with Diagnostic Electrodes, Far-Field Detection Electrodes, and Guidewire FIG. 3 is a schematic pictorial illustration of diagnostic balloon catheter 40 of FIG. 1, in accordance with an embodiment of the present invention. As seen, in the embodiments described by FIG. 3, balloon catheter 40 comprises a membrane 44 underlying expandable frame, such as expandable frame 39 described above, that comprises spines 45. Balloon 40 is fitted at the distal end of shaft 22. Inflatable balloon 40 has an exterior wall 43 of a bio-compatible material, for example, formed from a plastic such as polyethylene terephthalate (PET), polyurethane, or PEBAX®. Diagnostic electrodes 50 are disposed over an exterior face of PCB strips 45 in circumference over balloon 40.

At inset 51, the diagnostic electrodes 50 shown can come in contact with both tissue and surrounding blood, and hence, senses both near-field and far-field signals. The shown reference electrode 55 is located on a surface of the expandable frame substantially or generally opposite diagnostic electrode 50. Reference electrode 55 is electrically isolated from tissue, as described above. In an embodiment, the isolation is done by partially encapsulating electrode 55 in an insulating material, such as an epoxy resin or with another polymer-based sealant. Insulation may also be provided, or assisted, by using a water-resistant seal. Still, electrode 55 can only be in physical contact with surrounding blood (and thus in electrical contact with blood), through gaps 57, and acquires far-field bio-electric signals than propagate through blood from remote cardiac regions. As noted above, such far-field interfering bio-electric signals can therefore be subtracted from respective signals acquired by diagnostic electrode 50 to achieve a quality diagnostic signal.

As seen in FIG. 3, balloon 40 is fitted with a smooth, round, and hollow distal end 65 for membrane 44 of balloon 40 to slide on a guidewire 60. The balloon is also configured to have no protruding distal "knob," so that the whole structure is smooth, so as to minimally perturb tissue and blood flow. Thus, there is less chance of blood clot formation. Even with the thin guidewire 60, there are very few protuberances which may cause blood clots.

A balloon catheter having an internal distal end is described in U.S. Provisional patent application Ser. No. 15/857,101, filed Dec. 28, 2017, entitled "Balloon Catheter with Internal Distal End," which is assigned to the assignee of the present patent application and whose disclosure is incorporated herein by reference.

Figure 4:
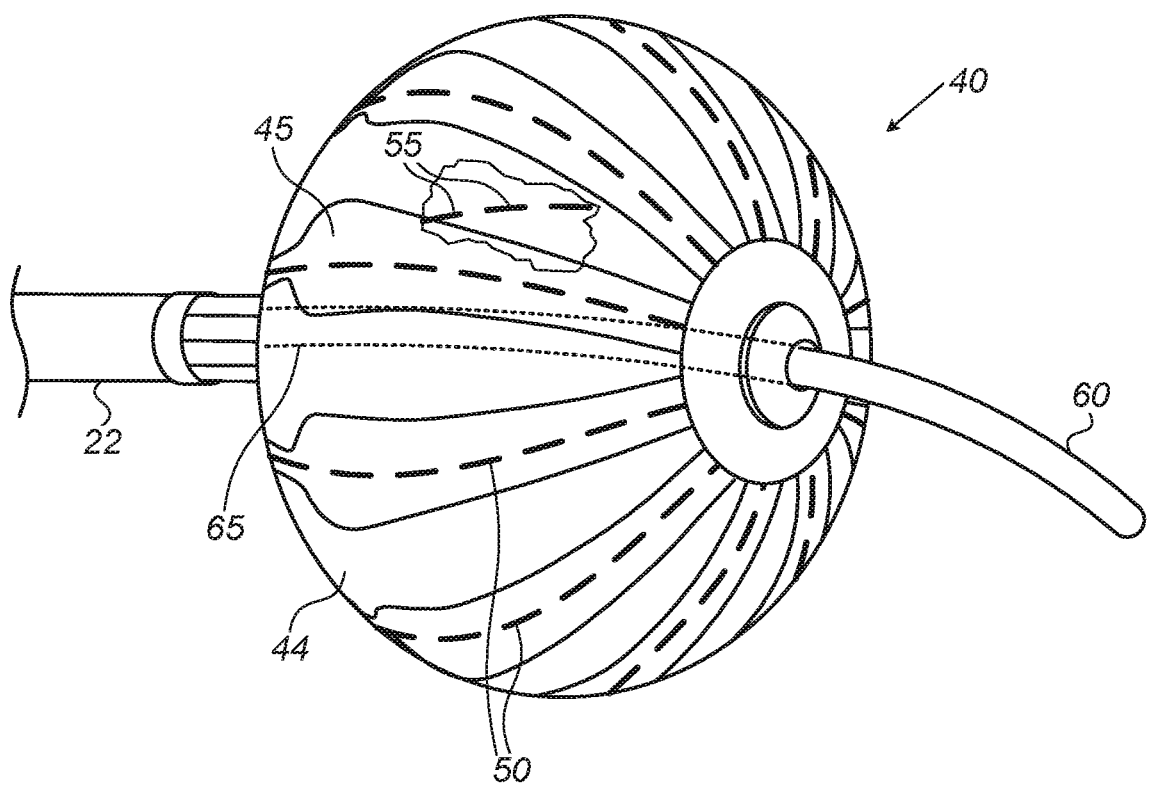
FIG. 4 is a pictorial volume rendering the diagnostic balloon of FIG. 3, in accordance with an embodiment of the present invention.

FIG. 4 is a pictorial volume rendering of diagnostic balloon 40 of FIG. 3, in accordance with an embodiment of the present invention. As seen in FIG. 4, the balloon is configured to be held distally by an internal flexible structure comprising distal end 65, so there is no need for a protruding distal end to fix the balloon to shaft 22, thereby keeping the whole structure smooth, and therefore minimally perturb tissue and blood flow. The balloon has a soft round distal end and can slide on guidewire 60. To allow for the sliding of balloon 40, hollow distal end 65 is designed to be moved on guidewire 60 either when the balloon is in a deflated form or when the balloon is in an inflated form.

In some embodiments, electrodes 50 are interconnected to create an intracardiac bi-polar electrode configuration. In another embodiment the electrodes sense signals relative to an external reference electrode, such as one of electrodes 27 attached to the skin.

As further seen in FIG. 4, opposing electrodes 55 can be distinguished as facing the balloon wall (the balloon wall and any sealant or adhesive are illustrated as transparent only to show electrodes 55).

The illustration shown in FIG. 4 is chosen purely for the sake of conceptual clarity. FIG. 4 shows only portions relevant to embodiments of the present invention. Other system elements, such as electrical wiring for the PCB, temperature sensors, and sealing elements, if required, are omitted.

Figure 5:
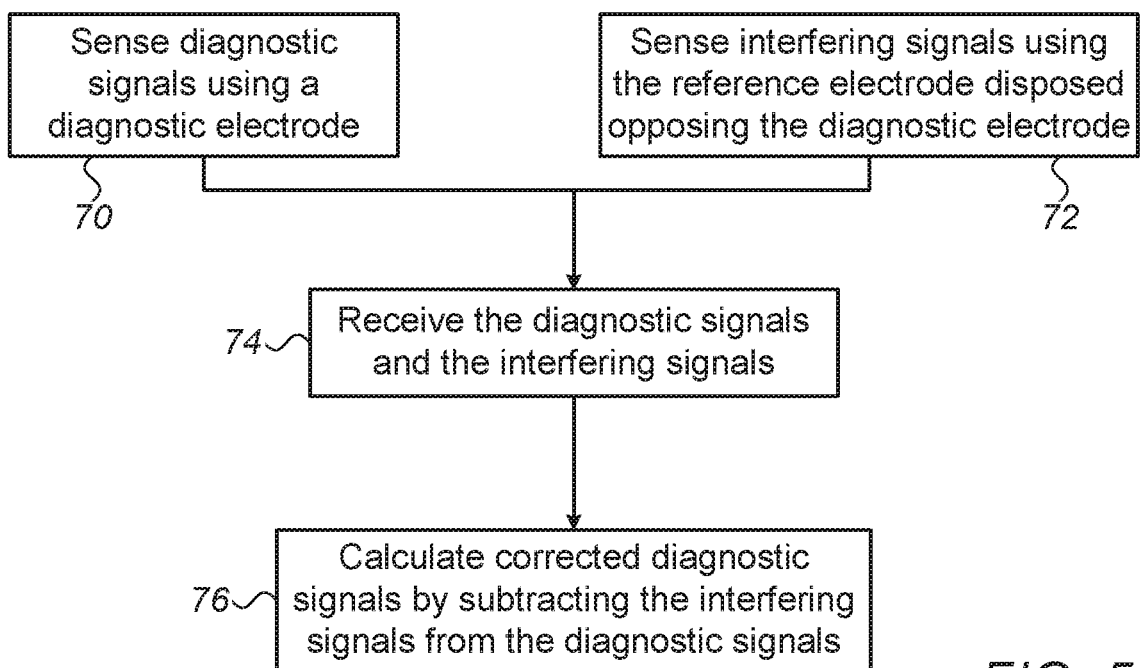
FIG. 5 is a flow chart that schematically illustrates a method for canceling interference in electrode pairs disposed over the diagnostic balloon of FIG. 3, in accordance with an embodiment of the present invention.

FIG. 5 is a flow chart that schematically illustrates a method for canceling interference per electrode pairs disposed over the diagnostic balloon of FIG. 3, in accordance with an embodiment of the present invention. The process begins with a diagnostic electrode, such as electrode 50, sensing diagnostic signals, at a diagnostic signals sensing step 70. In parallel, reference electrode 55 disposed opposing diagnostic electrode 50, senses interfering signals, at an interference sensing step 72. Next, processor 41 receives the diagnostic signals sensed by diagnostic electrode 50, and the interfering signals sensed by reference electrode 55, at a signal receiving step Finally, processor 41 calculates, using the dedicated algorithm, corrected diagnostic signals by subtracting the interfering signals from the diagnostic signals, at a signal calculation step 76.

Figure 2B:
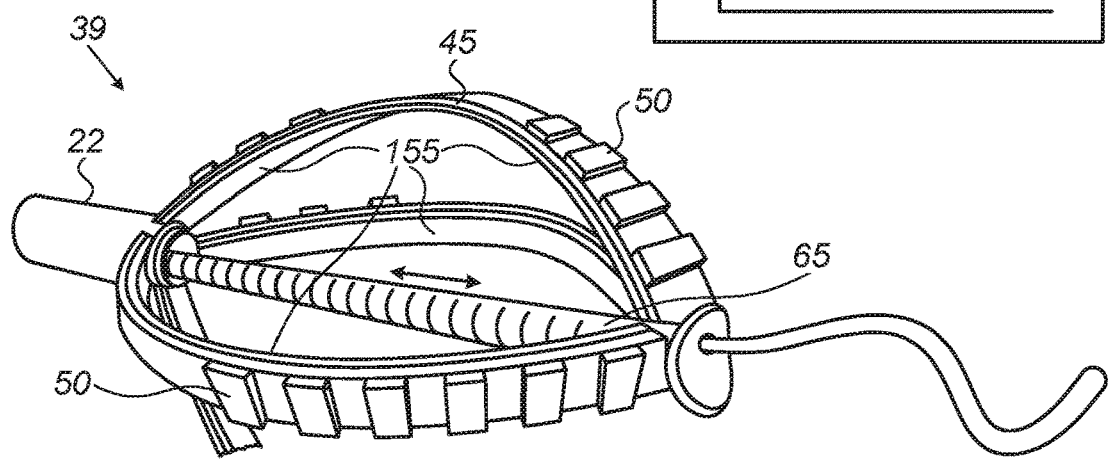

The example flow chart shown in FIG. 5 is chosen purely for the sake of conceptual clarity. Additional steps may be included, which are omitted for simplicity of presentation. For example, in an additional embodiment, the sensed signals are filtered prior to being received by processor 41. Based on the disclosure provided in this application, one skilled in the art would be able to create suitable software and obtain the necessary hardware to carry out the algorithm shown herein for various embodiments of the device shown in FIGS. 2-4.

While all embodiments described can be formed from flexible PCB electrical circuits, it is within the scope of the disclosure and invention to utilize thin-film technologies instead of flexible PCB such as the thin-film example as shown and described in WO 2015/117908 (entitled: MEDICAL DEVICE FOR ABLATING TISSUE CELLS AND SYSTEM COMPRISING A DEVICE OF THIS TYPE), which is hereby incorporated by reference into this application It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A medical apparatus, comprising:
a shaft extending along a longitudinal axis and configured to be inserted into an organ of a patient;
a flexible end effector disposed at a distal end of the shaft, the flexible end effector comprising a plurality of spines, each spine of the plurality of spines comprising:
a plurality of diagnostic electrodes disposed on a first side of the spine, the plurality of diagnostic electrodes each being configured to sense diagnostic signals when in contact with tissue;
and a reference electrode disposed on a second side of the spine opposite the diagnostic electrode, the reference electrode being electrically insulated from each diagnostic electrode of the plurality of diagnostic electrodes and the tissue and configured to sense interfering signals, the reference electrode being larger than each diagnostic electrode of the plurality of diagnostic electrodes.

2. The medical apparatus of claim 1, wherein the reference electrode extends from about a proximal end of the spine to about a distal end of the spine.

3. The medical apparatus of claim 1, wherein the reference electrode comprises a plurality of reference electrodes disposed on the second side of the spine and electrically connected to each other.

4. The medical apparatus of claim 3, wherein each reference electrode of the plurality of reference electrodes is larger than the diagnostic electrode.

5. The medical apparatus according to claim 1, wherein at least a portion of the spine is made of flexible printed circuit board (PCB), and wherein the diagnostic electrode and the reference electrode are disposed on opposing facets of the flexible PCB.

6. The medical apparatus of claim 5 further comprising a plurality of flexible printed circuit boards (PCBs); and
an inflatable membrane disposed in a volume defined by the PCBs, wherein the reference electrode is in contact with the inflatable membrane.

7. The medical apparatus according to claim 1, wherein the shaft is hollow along the longitudinal axis thereof, and wherein the medical apparatus further comprises a guidewire configured to be inserted through the shaft and to guide the flexible end effector toward a target location in the organ.

8. The medical apparatus according to claim 1, wherein the interfering signals comprise far-field bio-electrical signals.

9. The medical apparatus of claim 1, further comprising:
a processor, which is configured to: receive the diagnostic signals sensed by each diagnostic electrode of the plurality of diagnostic electrodes; receive the interfering signals sensed by the reference electrode; and calculate corrected diagnostic signals by subtracting the interfering signals from the diagnostic signals.

10. The medical apparatus of claim 9, wherein the reference electrode extends from about a proximal end of the flexible end effector to about a distal end of the flexible end effector.

11. The medical apparatus of claim 1, wherein the reference electrode is at least partially encapsulated in an electrically insulating material.

12. The medical apparatus of claim 11, wherein the electrically insulating material comprises a water-resistant seal.

13. A medical system, comprising:
 a flexible end effector disposed at a distal end of a shaft extending along a longitudinal axis, the flexible end effector comprising a plurality of spines, each spine of the plurality of spines comprising:
 a plurality of diagnostic electrodes disposed on a first side of the spine, each diagnostic electrode of the plurality of diagnostic electrodes being configured to sense diagnostic signals when in contact with tissue; and
 a reference electrode disposed on a second side of the spine opposite the plurality of diagnostic electrodes, the reference electrode being (1) electrically insulated from each diagnostic electrode of the plurality of diagnostic electrodes and the tissue, (2) larger than each diagnostic electrode of the plurality of diagnostic electrodes, and (3) configured to sense interfering signals; and a processor, which is configured to:
 receive the diagnostic signals sensed by at least one diagnostic electrode of the plurality of diagnostic electrodes;
 receive the interfering signals sensed by at least one reference electrode; and
 calculate corrected diagnostic signals by subtracting the interfering signals from the diagnostic signals.

14. The medical system of claim 13, wherein the reference electrode extends from about a proximal end of the spine to about a distal end of the spine.

15. The medical system of claim 13, wherein the flexible end effector is configured to transition between a collapsed state and an expanded state.

16. The medical system of claim 13, wherein the diagnostic electrode is at least partially encapsulated in an insulating material.

* * * * *